United States Patent
Combs

(10) Patent No.: US 10,188,541 B2
(45) Date of Patent: Jan. 29, 2019

(54) IMMOBILIZING SPLINTS

(71) Applicant: William Miles Combs, Lihue, HI (US)

(72) Inventor: William Miles Combs, Lihue, HI (US)

(*) Notice: Subject to any disclaimer, the term of this patent is extended or adjusted under 35 U.S.C. 154(b) by 342 days.

(21) Appl. No.: 15/003,513

(22) Filed: Jan. 21, 2016

(65) Prior Publication Data
US 2017/0209293 A1 Jul. 27, 2017

(51) Int. Cl.
A61F 5/05 (2006.01)
A61F 5/058 (2006.01)
A61F 5/042 (2006.01)
A61F 5/01 (2006.01)

(52) U.S. Cl.
CPC ........ *A61F 5/05858* (2013.01); *A61F 5/0118* (2013.01); *A61F 5/042* (2013.01); *A61F 5/05* (2013.01); *A61F 5/058* (2013.01); *A61F 5/05841* (2013.01); *A61F 5/0109* (2013.01)

(58) Field of Classification Search
CPC ........ A61F 5/0109; A61F 5/0118; A61F 5/05; A61F 5/058; A61F 5/05841; A61F 5/05858
USPC .................... 602/20; 128/877, 878
See application file for complete search history.

(56) References Cited

U.S. PATENT DOCUMENTS

| | | | |
|---|---|---|---|
| 3,719,187 A * | 3/1973 | Ulansey | A61F 5/05866 602/6 |
| 3,812,851 A | 5/1974 | Rodriguez | |
| 4,013,070 A | 3/1977 | Harroff | |
| 4,470,410 A | 9/1984 | Elliott | |
| 4,662,366 A | 5/1987 | Tari | |
| 4,941,479 A | 7/1990 | Russell et al. | |
| 5,728,053 A * | 3/1998 | Calvert | A61F 5/05858 128/877 |
| 5,832,928 A * | 11/1998 | Padilla, Jr. | A61M 25/02 128/877 |
| 6,000,402 A | 12/1999 | Able | |
| 7,182,088 B2 | 2/2007 | Jenkins | |
| 2014/0060547 A1* | 3/2014 | Vallino | A61F 5/05858 128/845 |
| 2015/0335831 A1* | 11/2015 | De Zayas | A61M 5/52 128/877 |

* cited by examiner

*Primary Examiner* — Keri J Nelson
(74) *Attorney, Agent, or Firm* — DASCENZO Intellectual Property Law, P.C.

(57) ABSTRACT

Immobilizing splints for antecubital intravenous injection sites. The splints include a flexible sleeve configured to be closed around an elbow of a patient, a preformed opening in the sleeve, at least one fastening member to close the sleeve around the elbow, and at least one stiffening member positioned in the sleeve proximal the preformed opening such that the at least one stiffening member is positioned on an anterior side of the arm when the sleeve is closed around the elbow.

20 Claims, 2 Drawing Sheets

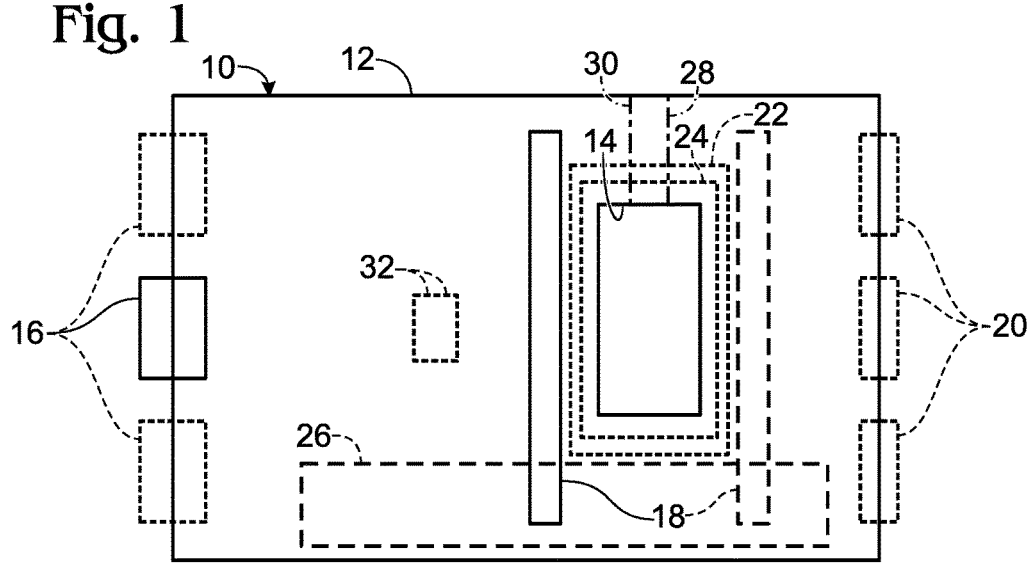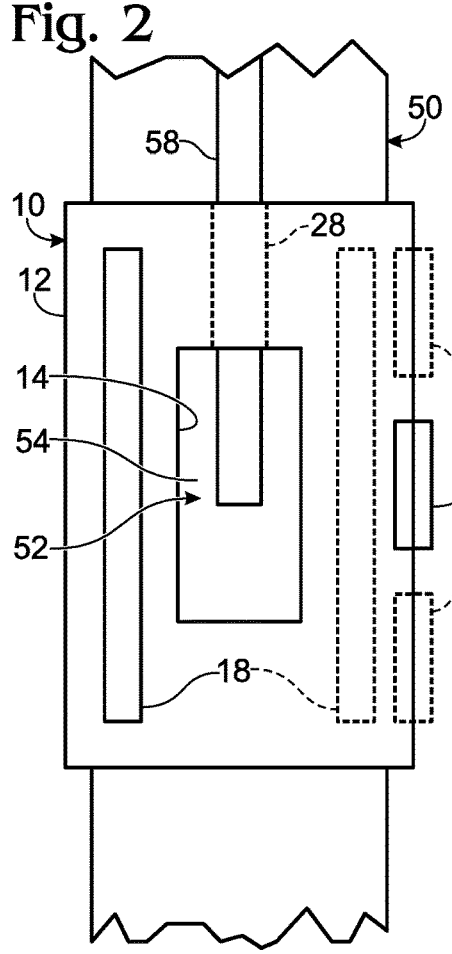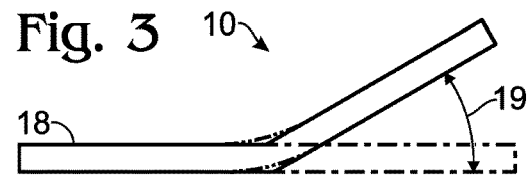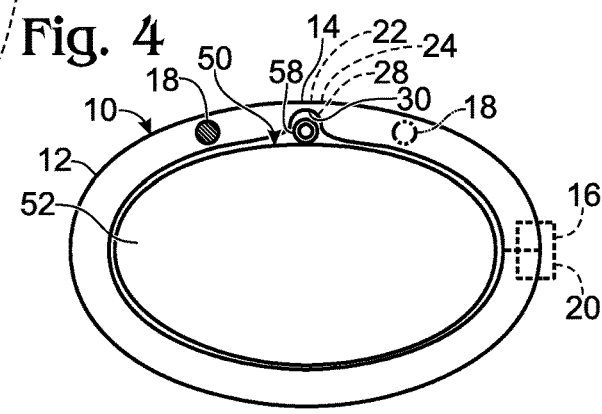

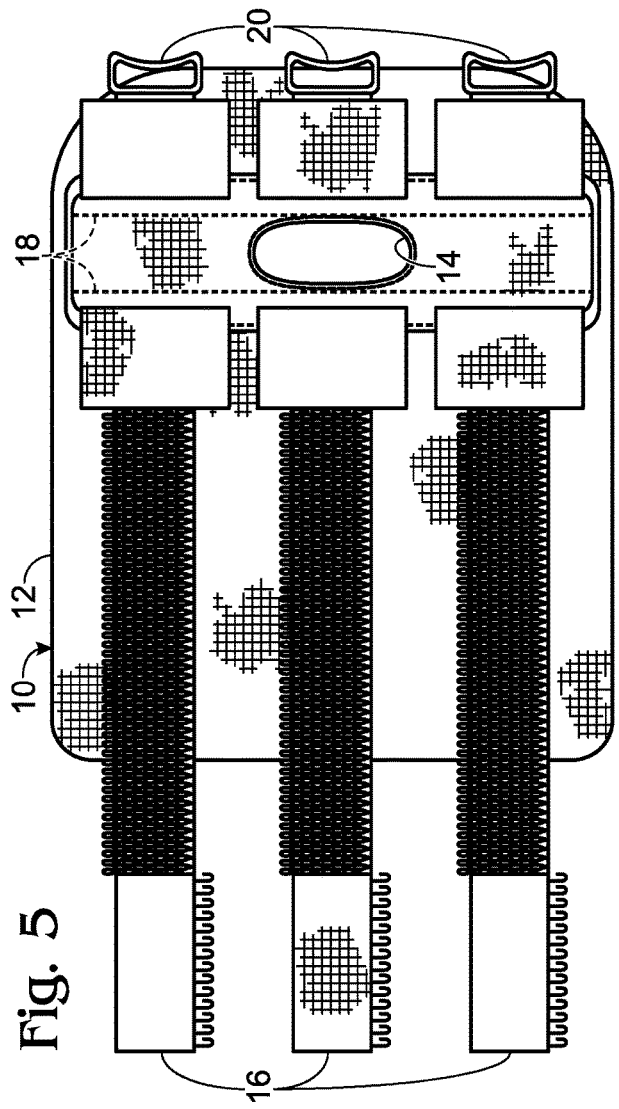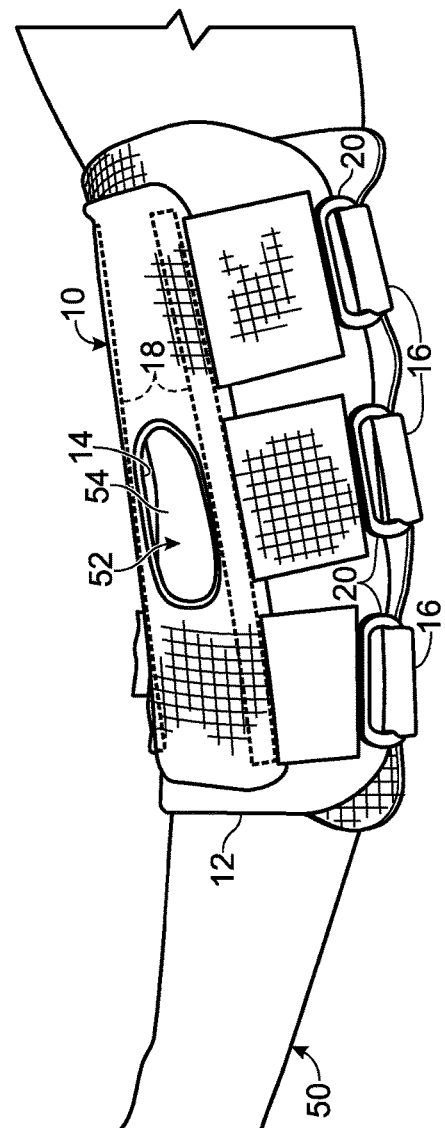

IMMOBILIZING SPLINTS

FIELD

The present disclosure relates generally to immobilizing splints.

BACKGROUND

Intravenous (IV) therapy allows for convenient and efficient administration of a drug to a patient by delivering the drug directly to the patient's bloodstream, for example via a needle inserted into the patient's median cubital vein at the elbow. However, IV therapy generally requires that an IV injection site remain undisturbed and that an IV supply tube supplying the drug to the injection site remain unkinked while the drug is being administered.

In some cases, the patient may be unwilling and/or unable to maintain the IV injection site and/or IV supply tube in an undisturbed state, such as if the patient is intoxicated or disobedient. In such a case, it may be beneficial to surround the IV injection site with an immobilizing splint. For example, when the IV injection site is an antecubital fossa of an arm, the immobilizing splint may include one or more stiffening members to prevent the patient from flexing the elbow in a manner that could disturb the IV injection site and/or the IV supply tube.

If the stiffening members of a splint are oriented laterally adjacent to the elbow or on a posterior side of the arm, they may not provide sufficient resistance to prevent flexure of the elbow. For example, the immobilizing splint may be formed of a flexible material that permits the elbow to flex to an undesirable degree despite the stiffening members remaining in an unbent configuration. Thus, there exists a need for an immobilizing splint that includes stiffening members that are appropriately configured and positioned to limit flexure of the elbow.

SUMMARY

Immobilizing splints for antecubital intravenous injection sites are disclosed herein. The immobilizing splints include a sleeve of flexible material configured to be closed around an elbow of a patient, a preformed opening in the sleeve configured to allow visual access to an antecubital fossa of the elbow, at least one fastening member configured to close the sleeve around the elbow, and at least one stiffening member configured to maintain the elbow in an at least substantially extended position. The at least one stiffening member is positioned in the sleeve proximal the preformed opening such that, when the sleeve is closed around the elbow, the at least one stiffening member is positioned on an anterior side of the arm.

BRIEF DESCRIPTION OF THE DRAWINGS

FIG. 1 is a schematic top view illustrating examples of an immobilizing splint according to the present disclosure in an open configuration.

FIG. 2 is a schematic top view illustrating examples of an immobilizing splint according to the present disclosure closed around a patient's limb.

FIG. 3 is a schematic side view illustrating examples of a stiffening member of an immobilizing splint according to the present disclosure.

FIG. 4 is a schematic end view illustrating examples of a portion of an immobilizing splint according to the present disclosure.

FIG. 5 is a top view illustration of an example of an immobilizing splint according to the present disclosure in an open configuration.

FIG. 6 is a top view illustration of an example of an immobilizing splint according to the present disclosure closed around a patient's limb.

DETAILED DESCRIPTION

FIGS. 1-6 provide examples of immobilizing splints 10 according to the present disclosure. Elements that serve a similar, or at least substantially similar, purpose are labeled with like numbers in each of FIGS. 1-6, and these elements may not be discussed herein with reference to each of FIGS. 1-6. Similarly, all elements may not be labeled in each of FIGS. 1-6, but reference numerals associated therewith may be utilized herein for consistency. Elements, components, and/or features that are discussed herein with reference to one or more of FIGS. 1-6 may be included in and/or utilized with any of FIGS. 1-6 without departing from the scope of the present disclosure.

In general, elements that are likely to be included in a given (i.e., a particular) embodiment are illustrated in solid lines, while elements that are optional to a given embodiment are illustrated in dashed lines. However, elements that are shown in solid lines are not essential to all embodiments, and an element shown in solid lines may be omitted from a given embodiment without departing from the scope of the present disclosure.

With reference to FIGS. 1-2, immobilizing splint 10 includes a sleeve 12 that may be configured to wrap around a patient's limb, such as an arm 50, to restrict bending of a corresponding joint, such as an elbow 52. As discussed herein, splint 10 is illustrated and primarily described in connection with use on a patient's arm to restrict bending of the arm at the elbow, but use of splint 10 is not restricted solely to use on such limbs and joints of a patient. Sleeve 12 may be formed of a flexible material, and may include a preformed opening 14. Preformed opening 14 may allow visual and/or physical access to an intravenous (IV) injection site 54 (as shown in FIG. 2), such as an antecubital fossa of elbow 52, when the sleeve is closed around the elbow. As used herein, the term "injection site" is intended to refer to a localized region of a limb, such as a region that includes a point at which an injection cannula may enter the limb. Thus, when splint 10 is operatively mounted on a patient's limb, preformed opening 14 may define, surround, and/or bound the injection site. Splint 10 additionally may include an opening cover 22 that is configured to selectively overlay and expose preformed opening 14, and/or may include a transparent window 24 that overlays preformed opening 14.

Splint 10 may include at least one fastening member 16 that may be configured to selectively close sleeve 12 around elbow 52. Splint 10 additionally may include at least one corresponding fastener receiver 20 to selectively couple or otherwise engage with the at least one fastening member 16 to selectively secure the splint in a closed configuration around elbow 52.

Splint 10 also may include at least one stiffening member 18 that may be configured to maintain the elbow in an at least substantially extended position, or even a fully extended position, when sleeve 12 is closed around elbow 52. As used herein, the term "extended position" may refer to an orientation of a bendable limb, such as elbow 52, in which the limb is at least substantially, or even completely, linear, unbent, and/or locked.

Stiffening member 18 may be positioned in sleeve 12 proximal preformed opening 14 such that, when the sleeve is closed around elbow 52 in a position that allows visual access to injection site 54 through preformed opening 14, stiffening member 18 is positioned on an anterior side of arm 50. For example, stiffening member 18 may be positioned at a distance from a nearest edge of preformed opening 14 that is less than 1 millimeter (mm), less than 2 mm, less than 3 mm, less than 5 mm, less than 10 mm, less than 15 mm, less than 20 mm, less than 30 mm, and/or less than 50 mm.

As discussed herein, splint 10 generally is described in the context of immobilizing elbow 52 of arm 50, and stiffening member 18 generally is discussed as being positioned on an anterior side of arm 50. However, this is not required to all embodiments, and it is within the scope of the present disclosure that splint 10 may be utilized to immobilize any suitable bendable limb, and such bendable limb may flex toward either an anterior or a posterior side of the bendable limb. Therefore, as used herein, the term "flexure side," may be used to describe the side of a bendable limb on which a joint is flexed. For example, the flexure side of a human's arm is the anterior side of the arm, with the arm's elbow flexing to pivot the arm's wrist toward and away from the arm's shoulder. As another example, the flexure side of a human's leg is the posterior side of the leg, with the leg's knee flexing to pivot the leg's foot toward and away from the leg's thigh. Therefore, references herein to the anterior side of an arm additionally or alternatively may refer to the flexure side of any bendable limb. Furthermore, references to stiffening member(s) 18 and/or preformed opening 14 extending against and/or proximate an anterior side of an arm additionally or alternatively may refer to the stiffening member(s) and/or the preformed opening extending against and/or proximate the flexure side of any bendable limb.

In an embodiment in which stiffening member 18 is positioned on an anterior/flexure side of arm 50, the stiffening member may resist a flexing of elbow 52 by directly impeding the flexing of the elbow. By contrast, a stiffening member that is not positioned on an anterior/flexure side of a limb may impede a flexing of the limb only indirectly, such as by resisting a deformation of sleeve 12. For example, in an embodiment of splint 10 that includes flexible sleeve 12 with stiffening member 18 oriented on a posterior (non-flexure) side of arm 50, a range of motion of elbow 52 may be limited by a flexibility of the sleeve rather than by a rigidity of the stiffening member.

Splint 10 additionally may include a terminal reinforced region 26 that is proximal a hand of the patient relative to a shoulder of the patient when the sleeve is closed around the elbow. Terminal reinforced region 26 may be configured to provide additional resistance against stretching and/or bending of splint 10 as a result of motion of the patient's hand and/or forearm. Specifically, terminal reinforced region 26 may have an increased thickness, rigidity, and/or stiffness relative to a remainder of splint 10 that does not include the terminal reinforced region and/or a longitudinal reinforced region 28. For example, terminal reinforced region 26 may include a material, such as a leather, that is more stiff and/or more rigid than a remainder of splint 10 that does not include the terminal reinforced region and/or the longitudinal reinforced region.

Splint 10 additionally may include longitudinal reinforced region 28, which is positioned adjacent to an IV supply tube 58 when sleeve 12 is closed around elbow 52. Longitudinal reinforced region 28 may be configured to maintain IV supply tube 58 in an unconstricted state to allow for an uninterrupted supply of fluid to IV injection site 54. Specifically, longitudinal reinforced region 28 may have an increased thickness, rigidity, and/or stiffness relative to a remainder of splint 10 that does not include the longitudinal reinforced region and/or terminal reinforced region 26. For example, longitudinal reinforced region 28 may include a material, such as a leather, that is more stiff and/or more rigid than a remainder of splint 10 that does not include the longitudinal reinforced region and/or the terminal reinforced region.

Splint 10 additionally may include at least one anchor point 32 that is configured to selectively couple to a restraint. For example, anchor point 32 may include a D-ring and/or a ladder-lock buckle and may be configured to receive and/or couple to a restraint to maintain the arm of the patient in a substantially fixed and/or constricted orientation relative to an external object such as a hospital bed. Splint 10 optionally may include a plurality of spaced-apart anchor points 32, such as at least one anchor point 32 at a proximal region of the splint (relative to a given end of splint 10 when sleeve 12 is closed around elbow 52) and at least one anchor point 32 at a distal region of the splint.

Splint 10 may be configured to be sufficiently stiff to prevent occlusion of the intravenous injection site. For example, splint 10 may be sufficiently stiff to prevent a kink in a portion of IV supply tube 58 that underlies splint 10 when sleeve 12 is closed around elbow 52. In particular, splint 10 may be sufficiently stiff to prevent elbow 52 from flexing by more than a maximum flex angle that is measured relative to a nominal (i.e., unflexed) configuration of the splint. For example, the maximum flex angle may be at least 5 degrees, at least 10 degrees, at least 15 degrees, at least 20 degrees, at least 30 degrees, at least 40 degrees, less than 45 degrees, less than 35 degrees, less than 25 degrees, less than 17 degrees, less than 12 degrees, less than 7 degrees, less than 3 degrees, and/or zero degrees.

Splint 10 may include more than one stiffening member 18. For example, splint 10 may include two stiffening members 18 that may be oriented on opposite sides of preformed opening 14. Stiffening member 18 may be at least substantially rigid, and/or may be at least partially bendable. Stiffening member 18 may include any appropriate material such as steel, aluminum, titanium, fiberglass, plastic, a polymer, a carbon fiber-reinforced polymer, nylon, wood, and/or combinations thereof. Splint 10 further may include more than two stiffening members 18. In some embodiments, splint 10 may be described as only including stiffening members(s) 18 on the flexure side of the limb, such as the anterior side of a human arm.

Stiffening member 18 may be characterized by a stiffening member length as measured along a longitudinal dimension of the stiffening member. For example, the stiffening member length may be at least 5 centimeters (cm), at least 10 cm, at least 15 cm, at least 20 cm, at least 25 cm, at least 30 cm, at least 35 cm, less than 40 cm, less than 37 cm, less than 32 cm, less than 27 cm, less than 22 cm, less than 17 cm, less than 12 cm, and/or less than 7 cm. Additionally or alternatively, the stiffening member length may be at least 50%, at least 60%, at least 70%, at least 80%, at least 90%, at least 100%, less than 115%, less than 105%, less than 95%, less than 85%, less than 75%, and/or less than 65% of a splint length that is measured in a direction at least substantially parallel to a longitudinal axis of stiffening member 18 when the stiffening member is included in the splint.

Stiffening member 18 additionally may be characterized by a stiffening member thickness as measured in a direction at least substantially perpendicular to the longitudinal axis of the stiffening member. For example, the stiffening member thickness may be at least 1 mm, at least 3 mm, at least 5 mm, at least 10 mm, less than 15 mm, less than 7 mm, less than 4 mm, and/or less than 2 mm.

Stiffening member 18 may be coupled to splint 10 by any appropriate construction. For example, stiffening member 18 be sewn into splint 10. Additionally or alternatively, stiffening member 18 may be configured to be selectively removable from splint 10. For example, sleeve 12 of splint 10 may include a preformed recess with a closed end into which stiffening member 18 may be inserted. An open end of the preformed recess subsequently may be sewn shut and/or selectively closed, such as by a hook-and-loop fastener or a snap closure, such that stiffening member 18 may be prevented from being unintentionally removed from splint 10.

Stiffening member 18 may have a shape that is at least substantially linear, or even completely linear, as shown in dash-dot lines in FIG. 3. Alternatively, and as illustrated in solid lines and in dash-dot-dot lines in FIG. 3, stiffening member 18 may include a preformed bend at a bend location that is substantially adjacent to elbow 52 when sleeve 12 is closed around the elbow. As illustrated in solid lines in FIG. 3, the preformed bend may be an abrupt bend in stiffening member 18; however, this is not required, and the preformed bend alternatively may be a gradual bend in stiffening member 18, as illustrated in dash-dot-dot lines in FIG. 3. Stated differently, the preformed bend may describe a curved region of stiffening member 18 that is curved away from a longitudinal axis of the stiffening member, and the curved region may represent any appropriate proportion of a total length of the stiffening member. For example, the curved region may have a length that is greater than 2%, greater than 5%, greater than 10%, greater than 20%, greater than 50%, less than 50%, less than 25%, less than 17%, less than 12%, less than 7%, and/or less than 3% of the total length of the stiffening member.

The preformed bend of the stiffening member may result in splint 10 having a nominal configuration that includes a corresponding splint bend, which may maintain elbow 52 in a more comfortable orientation when sleeve 12 is closed around the elbow. In particular, and with continued reference to FIG. 3, the preformed bend of stiffening member 18 may be characterized by a bend angle 19. As illustrated in FIG. 3, bend angle 19 may be measured from one end of stiffening member 18 to a projection of an opposite end of stiffening member 18 that is coaxial with the opposite end of stiffening member 18 (illustrated in dash-dot lines in FIG. 3). For example, bend angle 19 may be at least 5 degrees, at least 10 degrees, at least 15 degrees, at least 20 degrees, at least 30 degrees, at least 40 degrees, less than 45 degrees, less than 35 degrees, less than 25 degrees, less than 17 degrees, less than 12 degrees, less than 7 degrees, and/or less than 3 degrees.

As illustrated in FIG. 1, splint 10 may have a shape that is generally substantially rectangular when the splint is not secured around a patient's arm or other limb. Such a configuration may be referred to herein as an "open configuration" and/or an "unsecured configuration," and may refer to a configuration in which the splint is at least substantially, or even entirely, flat and/or unbent. However, it is not necessary that splint 10 have a shape that is generally substantially rectangular when in an open configuration, and the splint may have any appropriate shape. As discussed, splint 10 may be characterized by a splint length that is measured substantially parallel to arm 50 when sleeve 12 is closed around elbow 52. For example, the splint length may be at least 5 cm, at least 10 cm, at least 15 cm, at least 20 cm, at least 25 cm, at least 30 cm, at least 35 cm, less than 40 cm, less than 37 cm, less than 32 cm, less than 27 cm, less than 22 cm, less than 17 cm, less than 12 cm, and/or less than 7 cm.

Similarly, splint 10 may be characterized by a splint width that is measured substantially perpendicular to the splint length. For example, the splint width may be at least 5 cm, at least 10 cm, at least 15 cm, at least 20 cm, at least 25 cm, at least 30 cm, at least 35 cm, less than 40 cm, less than 37 cm, less than 32 cm, less than 27 cm, less than 22 cm, less than 17 cm, less than 12 cm, and/or less than 7 cm.

Sleeve 12 of splint 10 may be formed of any suitable flexible material. For example, the flexible material may include a foam, such as an open-cell foam, a closed-cell foam, a neoprene foam, and/or a polyurethane foam. The flexible material may include a hypoallergenic material, and/or may include an elastomer. The flexible material may include a fabric, such as cotton, linen, nylon, polyester, silk, elastane, and/or wool. Sleeve 12 may be characterized by a sleeve thickness, which may be at least 1 mm, at least 2 mm, at least 3 mm, at least 5 mm, at least 10 mm, less than 20 mm, less than 15 mm, less than 7 mm, less than 3.5 mm, less than 2.5 mm, and/or less than 1.5 mm.

FIG. 4 is a schematic illustration of an end-on view of an example of splint 10 that is closed around arm 50. With reference to FIG. 4, sleeve 12 may be described as including an interior sleeve side that faces arm 50 when sleeve 12 is closed around elbow 52. The interior sleeve side may include at least one preformed channel 30 that is configured to receive IV supply tube 58. Specifically, preformed channel 30 may be configured to maintain the intravenous supply tube in an unconstricted state by providing a cavity in which IV supply tube 58 may be seated. When splint 10 includes both longitudinal reinforced region 28 and preformed channel 30, longitudinal reinforced region 28 may include and/or define at least a portion of the preformed channel, or vice versa. Thus, the preformed channel, when present, may be sufficiently stiff and/or rigid to resist constriction of the portion of IV supply tube 58 received in preformed channel 30.

Preformed channel 30 may be characterized by a channel depth. For example, the channel depth may be at least 1 mm, at least 2 mm, at least 3 mm, at least 5 mm, at most 10 mm, at most 7 mm, and/or at most 4 mm. Additionally or alternatively, IV supply tube 58 may be characterized by a tube diameter, and the channel depth may be at least 50% of the tube diameter, at least 60% of the tube diameter, at least 70% of the tube diameter, at least 80% of the tube diameter, at least 90% of the tube diameter, and/or at least substantially equal to the tube diameter.

With continued reference to FIG. 4, splint 10 generally includes at least one stiffening member 18, which may be positioned in sleeve 12 on an anterior/flexure side of arm 50 when the sleeve is closed around elbow 52. As illustrated in dashed lines in FIG. 4, splint 10 may include a second stiffening member 18 positioned in sleeve 12 on an anterior/flexure side of arm 50 and on an opposite side of preformed opening 14 relative to the other stiffening member (illustrated in solid lines in FIG. 4).

In FIG. 4, space has been shown between the schematically illustrated outer surface of arm 50 and the interior surface of sleeve 12 to make it easier to view these elements in FIG. 4. In many embodiments, the interior surface of sleeve 12 will extend against most, if not all, of the patient's arm (inclusive of any clothing, bandage, etc. applied to the corresponding portion of the patient's arm), especially in the regions of the sleeve underlying fastening member 16 and/or fastener receiver 20. Additionally, fastening member 16 and fastener receiver 20 are illustrated in FIG. 4 in dashed lines to indicate that the position of the fastening member and the fastener receiver with respect to one another and/or with respect to sleeve 12 may vary. For example, while FIG. 4 schematically illustrates fastening member 16 and fastener receiver 20 as being located on a lateral side of arm 50 when sleeve 12 is closed around elbow 52, this is not required, and it is within the scope of the present disclosure that the fastening member and/or the fastener receiver may come together at any suitable position along sleeve 12. Additionally, FIG. 4 schematically illustrates sleeve 12 as abutting itself as it closes around elbow 52 in dashed line; however, this is not required, and it is within the scope of the present disclosure that sleeve 12 may overlap itself as it closes around elbow 52 and/or that the sleeve may not fully enclose the elbow.

As discussed, and with reference to FIGS. 1-2 and 5-6, splint 10 may include preformed opening 14 that is configured to permit visual and/or physical access to IV injection site 54 when sleeve 12 is closed around elbow 52. Preformed opening 14 may have a presized perimeter, which may have a closed and continuous perimeter shape. Stated another way, preformed opening 14 may have an opening shape that is a single, simply connected shape. The perimeter shape may be any appropriate shape, such as a circle, an ellipse, a square, a rectangle, and/or a rounded rectangle.

Preformed opening 14 may be characterized by an opening length that is measured substantially parallel to arm 50 when sleeve 12 is closed around elbow 52. For example, the opening length may be at least 1 cm, at least 3 cm, at least 5 cm, at least 10 cm, less than 20 cm, less than 15 cm, less than 13 cm, less than 8 cm, less than 4 cm, and/or less than 2 cm. Additionally or alternatively, preformed opening 14 may be characterized by an opening width that is measured substantially perpendicular to arm 50 when sleeve 12 is closed around elbow 52. For example, the opening width may be at least 0.5 cm, at least 1 cm, at least 3 cm, at least 5 cm, less than 10 cm, less than 7 cm, less than 4 cm, and/or less than 2 cm.

As illustrated in FIG. 6, preformed opening 14 may expose a void near elbow 52 when sleeve 12 is closed around the elbow. Stated differently, portions of the interior sleeve side of sleeve 12 may not contact arm 50 at all times, for example when stiffening member 18 does not include the preformed bend. Additionally, it may be possible to bend arm 50 at elbow 52 through a small angle even when stiffening member 18 does not include the preformed bend, such as within a maximum flex angle. However, such cases may not adversely affect a capability of splint 10 to prevent a flexure of arm 50 of a sufficient degree to interrupt a flow through IV supply tube 58 and/or otherwise disturb IV injection site 54. That is, it is within the scope of the present disclosure that splint 10 may be configured to permit a flexure of arm 50 through a small angle without compromising a functionality of the splint. Furthermore, a properly installed splint 10 may restrict flexing of the elbow or other limb beyond a maximum flex angle even if there are portions of the interior sleeve side of sleeve 12 that are spaced apart from the patient's arm. In some embodiments, all of the interior sleeve side of sleeve 12 may contact arm 10 when splint 10 is properly installed in a closed configuration around the patient's elbow.

As discussed, splint 10 may include at least one fastening member 16 to operatively secure sleeve 12 around elbow 52. For example, fastening member 16 may include a strap that is configured to close sleeve 12 around elbow 52. Fastening member 16 may be configured to wrap around splint 10 when sleeve 12 is closed around elbow 52 and/or to selectively fasten to itself utilizing a temporary fastener such as a hook-and-loop fastener, a notched belt fastener, and/or a buckle. When fastening member 16 includes a hook-and-loop fastener, sleeve 12 may include a complementary hook-and-loop fastening surface such that fastening member 16 may selectively engage with any appropriate portion of sleeve 12. Additionally or alternatively, when splint 10 includes one or more fastener receivers 20, fastening member 16 may include a strap that is configured to be inserted into a corresponding fastener receiver 20 in the form of a strap loop as illustrated in FIGS. 5-6. Specifically, fastening member 16 may be inserted into and through fastener receiver 20 and drawn back upon itself in order to more effectively tighten sleeve 12 around elbow 52 and/or to prevent fastening member 16 from obstructing preformed opening 14.

Alternatively, fastening member 16 may not include a strap, and instead may include a fastening structure that is incorporated into sleeve 12. For example, fastening member 16 may include a component of a hook-and-loop fastener incorporated along a length of an edge of sleeve 12, and fastener receiver 20 may include a corresponding component of the hook-and-loop fastener incorporated along a length of an opposite edge of the sleeve. Additionally or alternatively, fastening member 16 and/or fastener receiver 20 may include one or more snaps, buttons, and/or other fasteners incorporated along a length of one or more edges of sleeve 12.

As illustrated in FIGS. 1-2 and 5-6, fastening member 16 and fastener receiver 20 may be positioned on opposite sides of preformed opening 14. However, this is not required, and it is within the scope of the present disclosure that the fastening member and/or the fastener receiver be positioned in any appropriate configuration. Similarly, fastening member 16 may be affixed to sleeve 12 at any appropriate location. For example, and as illustrated in FIGS. 5-6, fastening member 16 may be affixed to sleeve 12 at a location proximal preformed opening 14 relative to an end of the sleeve that wraps around elbow 52.

When fastening member 16 includes a strap, the strap may be characterized by a strap length, which may be at least 5 cm, at least 10 cm, at least 15 cm, at least 20 cm, at least 25 cm, at least 30 cm, at least 35 cm, less than 40 cm, less than 37 cm, less than 32 cm, less than 27 cm, less than 22 cm, less than 17 cm, less than 12 cm, and/or less than 7 cm. Similarly, the strap may be characterized by a strap width, which may be at least 0.5 cm, at least 1 cm, at least 1.5 cm, at least 2 cm, at least 3 cm, less than 5 cm, less than 4 cm, less than 3.5 cm, less than 2.5 cm, less than 1.75 cm, less than 1.25 cm, and/or less than 0.75 cm.

Splint 10 may include any suitable number of fastening members 16. For example, when each fastening member 16 includes a strap, splint 10 may include one strap, two straps, at least two straps, three straps, four straps, five straps, and/or more than five straps, and additionally may include a corresponding plurality of fastener receivers 20. When splint 10 includes more than one strap, the straps may be at least substantially, or even exactly, evenly distributed along a length of the splint as measured in a direction at least substantially parallel to arm 50 when sleeve 12 is closed around elbow 52. Additionally or alternatively, when splint 10 includes more than one fastener receiver 20, each fastener receiver may be laterally aligned with a corresponding strap and/or may be at least substantially, or even exactly, evenly distributed along a length of the splint on an opposite side of the splint relative to fastening members 16.

As discussed, and with reference to FIG. 1, splint 10 may include opening cover 22 that is configured to selectively overlay and expose preformed opening 14. Opening cover 22 may provide additional protection to IV injection site 54, for example to protect the injection site from a physical disturbance. Opening cover 22 may include, or be, a piece of material (such as a material included in sleeve 12) and may have dimensions generally similar to those of preformed opening 14. Opening cover 22 may be operable between an open position, in which the opening cover does not overlay or obstruct preformed opening 14, and a closed position, in which the opening cover overlays the preformed opening and/or protects IV injection site 54 from a physical disturbance. Opening cover 22 may include any suitable closure mechanism, such as a hook-and-loop fastener, to selectively retain the opening cover in at least a closed position. For example, an edge of opening cover 22 may be affixed to splint 10 such that the opening cover may pivot about the affixed edge. Alternatively, opening cover 22 may be entirely detachable from splint 10.

Similarly, as discussed and with reference to FIG. 1, splint 10 may include transparent window 24 that overlays preformed opening 14. When splint 10 includes opening cover 22, transparent window 24 may be positioned underneath opening cover 22 when sleeve 12 is closed around elbow 52. Alternatively, transparent window 24 may be incorporated into opening cover 22. Transparent window 24 may be configured to permit visual inspection of IV injection site 54 while simultaneously protecting the injection site from a physical disturbance. Transparent window 24 may be formed of any suitable material, such as an optically transparent plastic. Transparent window 24 may be attached to splint 10 at any appropriate location. For example, transparent window 24 may be attached to splint 10 distal preformed opening 14 relative to arm 50 when sleeve 12 is closed around elbow 52, or may be attached to the splint proximal the preformed opening relative to the arm when the sleeve is closed around the elbow.

As discussed herein, splint 10 generally is described in the context of immobilizing an elbow 52 of an arm 50. However, this is not required, and it is within the scope of the present disclosure that splint 10 may be utilized to immobilize any suitable limb and/or appendage, such as a leg, a finger, a wrist, and/or an ankle. Additionally, as discussed herein, splint 10 generally is described in the context of immobilizing a bendable limb of a human patient. However, this is not required, and it is within the scope of the present disclosure that splint 10 alternatively may be utilized to immobilize a bendable limb of a non-human patient, such as a domesticated pet or other animal. Furthermore, as discussed herein, splint 10 generally is described in the context of immobilizing a limb to protect an IV injection site; however, this is not required, and it is within the scope of the present disclosure that splint 10 additionally or alternatively may be utilized to immobilize a limb in any suitable medical or non-medical application. For example, in athletic activities such as rock climbing, it may be desirable during training to limit and/or prevent the flexure of a bendable limb, such as an elbow of an arm, and splint 10 may be utilized in such a context.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

Illustrative, non-exclusive examples of immobilizing splints according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

A1. An immobilizing splint for an antecubital intravenous injection site, the splint comprising:
 a sleeve of a flexible material configured to be selectively and removably closed around an elbow of an arm of a patient;
 a preformed opening in the sleeve configured to allow visual access to an antecubital fossa of the elbow;
 at least one fastening member configured to close the sleeve around the elbow; and
 at least one stiffening member configured to maintain the elbow in an at least substantially extended position when the sleeve is closed around the elbow, wherein the at least one stiffening member is positioned in the sleeve proximal the preformed opening such that, when the sleeve is closed around the elbow in a position that allows visual access to the antecubital fossa through the preformed opening, the at least one stiffening member is positioned on an anterior side of the arm.

A2. The splint of paragraph A1, wherein the splint is sufficiently stiff to prevent occlusion of the intravenous injection site.

A3. The splint of any of paragraphs A1-A2, wherein the splint is sufficiently stiff to prevent a kink in a portion of an intravenous supply tube that underlies the splint when the sleeve is closed around the elbow.

A4. The splint of any of paragraphs A1-A3, wherein the splint is sufficiently stiff to prevent the elbow from flexing by more than a maximum flex angle that is measured relative to a nominal configuration of the splint.

A5. The splint of paragraph A4, wherein the maximum flex angle is at least 5 degrees, at least 10 degrees, at least 15 degrees, at least 20 degrees, at least 30 degrees, at least 40 degrees, less than 45 degrees, less than 35 degrees, less than 25 degrees, less than 17 degrees, less than 12 degrees, and/or less than 7 degrees.

A6. The splint of any of paragraphs A1-A5, wherein the splint includes two stiffening members.

A7. The splint of paragraph A6, wherein the two stiffening members are oriented on opposite sides of the preformed opening.

A8. The splint of any of paragraphs A1-A7, wherein the at least one stiffening member is at least substantially rigid.

A9. The splint of any of paragraphs A1-A8, wherein the at least one stiffening member is at least partially bendable.

A10. The splint of any of paragraphs A1-A9, wherein the at least one stiffening member includes steel, aluminum, titanium, fiberglass, plastic, a polymer, a carbon fiber-reinforced polymer, nylon, and/or wood.

A11. The splint of any of paragraphs A1-A10, wherein the at least one stiffening member has a stiffening member length, and wherein the stiffening member length is at least 5 cm, at least 10 cm, at least 15 cm, at least 20 cm, at least 25 cm, at least 30 cm, at least 35 cm, less than 40 cm, less than 37 cm, less than 32 cm, less than 27 cm, less than 22 cm, less than 17 cm, less than 12 cm, and/or less than 7 cm.

A12. The splint of any of paragraphs A1-A11, wherein the at least one stiffening member has a/the stiffening member length, and wherein the stiffening member length is at least 50%, at least 60%, at least 70%, at least 80%, at least 90%, at least 100%, less than 115%, less than 105%, less than 95%, less than 85%, less than 75%, and/or less than 65% of a splint length.

A13. The splint of any of paragraphs A1-A12, wherein the at least one stiffening member has a stiffening member thickness, and wherein the stiffening member thickness is at least 1 millimeter (mm), at least 3 mm, at least 5 mm, at least 10 mm, less than 15 mm, less than 7 mm, less than 4 mm, and/or less than 2 mm.

A14. The splint of any of paragraphs A1-A13, wherein the at least one stiffening member is sewn in to the splint.

A15. The splint of any of paragraphs A1-A14, wherein the at least one stiffening member is removably attached to the splint.

A16. The splint of any of paragraphs A1-A15, wherein the at least one stiffening member is substantially linear.

A17. The splint of any of paragraphs A1-A16, wherein the at least one stiffening member includes a preformed bend at a bend location that is substantially adjacent to the elbow when the sleeve is closed around the elbow.

A18. The splint of paragraph A17, wherein the preformed bend has a bend angle, and further wherein the bend angle is at least 5 degrees, at least 10 degrees, at least 15 degrees, at least 20 degrees, at least 30 degrees, at least 40 degrees, less than 45 degrees, less than 35 degrees, less than 25 degrees, less than 17 degrees, less than 12 degrees, and/or less than 7 degrees.

A19. The splint of any of paragraphs A1-A18, wherein the splint is substantially rectangular when in an open configuration in which the splint is not closed around a patient's limb.

A20. The splint of any of paragraphs A1-A19, wherein the splint has a/the splint length that is measured substantially parallel to the arm when the sleeve is closed around the elbow, and further wherein the splint length is at least 5 centimeters (cm), at least 10 cm, at least 15 cm, at least 20 cm, at least 25 cm, at least 30 cm, at least 35 cm, less than 40 cm, less than 37 cm, less than 32 cm, less than 27 cm, less than 22 cm, less than 17 cm, less than 12 cm, and/or less than 7 cm.

A21. The splint of paragraph A20, wherein the splint has a splint width that is measured substantially perpendicular to the splint length, and further wherein the splint width is at least 5 cm, at least 10 cm, at least 15 cm, at least 20 cm, at least 25 cm, at least 30 cm, at least 35 cm, less than 40 cm, less than 37 cm, less than 32 cm, less than 27 cm, less than 22 cm, less than 17 cm, less than 12 cm, and/or less than 7 cm.

A22. The splint of any of paragraphs A1-A21, wherein the flexible material includes a hypoallergenic material.

A23. The splint of any of paragraphs A1-A22, wherein the flexible material includes a foam.

A24. The splint of paragraph A23, wherein the flexible material includes an open-cell foam.

A25. The splint of any of paragraphs A23-A24, wherein the flexible material includes a closed-cell foam.

A26. The splint of any of paragraphs A23-A25, wherein the flexible material includes a neoprene foam.

A27. The splint of any of paragraphs A23-A26, wherein the flexible material includes a polyurethane foam.

A28. The splint of any of paragraphs A1-A27, wherein the flexible material includes an elastomer.

A29. The splint of any of paragraphs A1-A28, wherein the flexible material includes a fabric.

A30. The splint of paragraph A29, wherein the fabric includes cotton, linen, nylon, polyester, silk, elastane, and/or wool.

A31. The splint of any of paragraphs A1-A30, wherein the sleeve has a sleeve thickness, and wherein the sleeve thickness is at least 1 mm, at least 2 mm, at least 3 mm, at least 5 mm, at least 10 mm, less than 20 mm, less than 15 mm, less than 7 mm, less than 3.5 mm, less than 2.5 mm, and/or less than 1.5 mm.

A32. The splint of any of paragraphs A1-A32, wherein the at least one fastening member includes at least one strap to close the sleeve around the elbow.

A33. The splint of paragraph A32, wherein the at least one strap has a strap length, and wherein the strap length is at least 5 cm, at least 10 cm, at least 15 cm, at least 20 cm, at least 25 cm, at least 30 cm, at least 35 cm, less than 40 cm, less than 37 cm, less than 32 cm, less than 27 cm, less than 22 cm, less than 17 cm, less than 12 cm, and/or less than 7 cm.

A34. The splint of any of paragraphs A32-A33, wherein the at least one strap has a strap width, and wherein the strap width is at least 0.5 cm, at least 1 cm, at least 1.5 cm, at least 2 cm, at least 3 cm, less than 5 cm, less than 4 cm, less than 3.5 cm, less than 2.5 cm, less than 1.75 cm, less than 1.25 cm, and/or less than 0.75 cm.

A35. The splint of any of paragraphs A32-A34, wherein the at least one strap includes a hook-and-loop fastener.

A36. The splint of any of paragraphs A32-A35, wherein the at least one strap includes a notched belt fastener.

A37. The splint of any of paragraphs A32-A36, wherein the at least one strap includes a buckle.

A38. The splint of any of paragraphs A32-A37, wherein the splint further includes at least one strap loop corresponding to the at least one strap, and further wherein the at least one strap is configured to be inserted into the at least one strap loop to close the sleeve around the elbow.

A39. The splint of any of paragraphs A32-A38, wherein the splint includes at least two straps.

A40. The splint of any of paragraphs A32-A38, wherein the splint includes one strap, two straps, three straps, four straps, five straps, and/or more than five straps.

A41. The splint of any of paragraphs A1-A40, wherein the preformed opening has an opening length that is measured substantially parallel to the arm when the sleeve is closed around the elbow, and further wherein the opening length is at least 1 cm, at least 3 cm, at least 5 cm, at least 10 cm, less than 20 cm, less than 15 cm, less than 13 cm, less than 8 cm, less than 4 cm, and/or less than 2 cm.

A42. The splint of any of paragraphs A1-A41, wherein the preformed opening has an opening width that is measured substantially perpendicular to the arm when the sleeve is closed around the elbow, and further wherein the opening width is at least 0.5 cm, at least 1 cm, at least 3 cm, at least 5 cm, less than 10 cm, less than 7 cm, less than 4 cm, and/or less than 2 cm.

A43. The splint of any of paragraphs A1-A41, wherein the preformed opening has a presized perimeter.

A44. The splint of paragraph A43, wherein the presized perimeter has a closed and continuous perimeter shape.

A45. The splint of paragraph A44, wherein the perimeter shape is a circle.

A46. The splint of any of paragraphs A44-A45, wherein the perimeter shape is an ellipse.

A47. The splint of any of paragraphs A44-A46, wherein the perimeter shape is a rectangle.

A48. The splint of any of paragraphs A44-A47, wherein the perimeter shape is a rounded rectangle.

A49. The splint of any of paragraphs A1-A48, wherein the splint further includes an opening cover that is configured to selectively overlay the preformed opening when the opening cover is in a closed position and to expose the preformed opening when the opening cover is in an open position.

A50. The splint of paragraph A49, wherein the cover includes a hook-and-loop fastener to selectively retain the opening cover in at least the closed position.

A51. The splint of any of paragraphs A1-A50, wherein the splint further includes a transparent window that overlays the preformed opening.

A52. The splint of paragraph A51, wherein the transparent window is formed of an optically transparent plastic.

A53. The splint of any of paragraphs A51-A52, wherein the transparent window is attached to the splint distal the preformed opening relative to the arm when the sleeve is closed around the elbow.

A54. The splint of any of paragraphs A51-A52, wherein the transparent window is attached to the splint proximal the preformed opening relative to the arm when the sleeve is closed around the elbow.

A55. The splint of any of paragraphs A1-A54, wherein the splint further includes a terminal reinforced region that is proximal a hand of the patient relative to a shoulder of the patient when the sleeve is closed around the elbow, wherein the terminal reinforced region has an increased thickness, rigidity, and/or stiffness relative to a remainder of the splint that does not include the terminal reinforced region.

A56. The splint of any of paragraphs A1-A55, wherein the splint further includes a longitudinal reinforced region that is positioned adjacent to an/the intravenous supply tube when the sleeve is closed around the elbow and is configured to maintain the intravenous supply tube in an unconstricted state, wherein the longitudinal reinforced region has an increased thickness, rigidity, and/or stiffness relative to a remainder of the splint that does not include the longitudinal reinforced region.

A57. The splint of any of paragraphs A1-A56, wherein the sleeve further includes an interior sleeve side that faces the arm when the sleeve is closed around the elbow, and further wherein the interior sleeve side includes at least one preformed channel that is configured to receive an/the intravenous supply tube.

A58. The splint of paragraph A57, wherein the preformed channel has a channel depth, wherein the intravenous supply tube has a tube diameter, and further wherein the channel depth is at least 50% of the tube diameter, at least 60% of the tube diameter, at least 70% of the tube diameter, at least 80% of the tube diameter, at least 90% of the tube diameter, and/or at least substantially equal to the tube diameter.

A59. The splint of any of paragraphs A57-A58, wherein the preformed channel has a/the channel depth, and further wherein the channel depth is at least 1 mm, at least 2 mm, at least 3 mm, at least 5 mm, at most 10 mm, at most 7 mm, and/or at most 4 mm.

A60. The splint of any of paragraphs A1-A59, wherein the splint further includes at least one anchor point configured to selectively couple to a restraint, and optionally wherein the splint further includes a plurality of spaced-apart anchor points.

A61. The splint of paragraph A60, wherein the at least one anchor point includes a D-ring.

A62. The splint of any of paragraphs A60-A61, wherein the at least one anchor point includes a ladder-lock buckle.

INDUSTRIAL APPLICABILITY

The immobilizing splints disclosed herein are applicable to the healthcare industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, when the disclosure, the preceding numbered paragraphs, or subsequently filed claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. An immobilizing splint for an antecubital intravenous injection site, the splint comprising:
   a sleeve of a flexible foam material configured to be selectively and removably closed around an elbow of an arm of a patient;
   a preformed opening in the sleeve configured to allow visual access to an antecubital fossa of the elbow, wherein the preformed opening has a presized perimeter that is closed and continuous;
   at least two straps configured to close the sleeve around the elbow, wherein each strap of the at least two straps includes a hook-and-loop fastener; and
   two stiffening members configured to maintain the elbow in an at least substantially extended position when the sleeve is closed around the elbow to prevent a kink in a portion of an intravenous supply tube that underlies the splint when the sleeve is closed around the elbow, wherein the stiffening members are positioned in the sleeve on opposite sides of the preformed opening such that, when the sleeve is closed around the elbow in a position that allows visual access to the antecubital fossa through the preformed opening, the stiffening members are positioned on an anterior side of the arm.

2. An immobilizing splint for an antecubital intravenous injection site, the splint comprising:
   a sleeve of a flexible material configured to be selectively and removably closed around an elbow of an arm of a patient;
   a preformed opening in the sleeve configured to allow visual access to an antecubital fossa of the elbow, wherein the preformed opening has a presized perimeter that is closed and continuous;
   at least one fastening member configured to close the sleeve around the elbow; and
   at least one stiffening member configured to maintain the elbow in an at least substantially extended position when the sleeve is closed around the elbow to prevent occlusion of the intravenous injection site, wherein the at least one stiffening member is positioned in the sleeve proximal the preformed opening such that, when the sleeve is closed around the elbow in a position that allows visual access to the antecubital fossa through the preformed opening, the at least one stiffening member is positioned on an anterior side of the arm.

3. The splint of claim 2, wherein the splint includes two stiffening members oriented on opposite sides of the preformed opening.

4. The splint of claim 2, wherein the splint is sufficiently stiff to prevent the elbow from flexing by more than a maximum flex angle that is measured relative to a nominal configuration of the splint.

5. The splint of claim 4, wherein the maximum flex angle is less than 12 degrees.

6. The splint of claim 2, wherein the at least one stiffening member includes a preformed bend at a bend location that is substantially adjacent to the elbow when the sleeve is closed around the elbow.

7. The splint of claim 6, wherein the preformed bend has a bend angle, and further wherein the bend angle is at least 5 degrees and less than 45 degrees.

8. The splint of claim 2, wherein the at least one stiffening member is formed of fiberglass.

9. The splint of claim 2, wherein the at least one stiffening member has a stiffening member length, wherein the stiffening member length is at least 70% of a splint length, wherein the at least one stiffening member has a stiffening member thickness, and wherein the stiffening member thickness is at least 3 mm and less than 15 mm.

10. The splint of claim 2, wherein the flexible material includes at least one of a hypoallergenic material or a neoprene foam.

11. The splint of claim 2, wherein the at least one fastening member includes at least one strap configured to selectively close the sleeve around the elbow, and further wherein the splint further includes at least one strap loop corresponding to the at least one strap, and further wherein the at least one strap is configured to be inserted into the at least one strap loop to close the sleeve around the elbow.

12. The splint of claim 11, wherein the splint includes at least two straps and at least two corresponding strap loops.

13. The splint of claim 2, wherein the splint further includes a transparent window that overlays the preformed opening.

14. The splint of claim 2, wherein the splint further includes a terminal reinforced region that is proximal a hand of the patient relative to a shoulder of the patient when the sleeve is closed around the elbow, wherein the terminal reinforced region has at least one of an increased thickness, an increased rigidity, and an increased stiffness relative to a remainder of the splint that does not include the terminal reinforced region.

15. The splint of claim 2, wherein the splint further includes a longitudinal reinforced region that is positioned adjacent to an intravenous supply tube when the sleeve is closed around the elbow and is configured to maintain the intravenous supply tube in an unconstricted state, wherein the longitudinal reinforced region has at least one of an increased thickness, an increased rigidity, and an increased stiffness relative to a remainder of the splint that does not include the longitudinal reinforced region.

16. The splint of claim 2, wherein the sleeve further includes an interior sleeve side that faces the win when the sleeve is closed around the elbow, and further wherein the interior sleeve side includes at least one preformed channel that is configured to receive an intravenous supply tube.

17. The splint of claim 2, further comprising an opening cover that is configured to be selectively operable in an open position and a closed position, wherein, in the open position, the opening cover is positioned such that the antecubital fossa is exposed via the preformed opening, and wherein, in the closed position, the opening cover overlays the preformed opening.

18. The splint of claim 2, wherein the presized perimeter of the preformed opening is closed and continuous when the splint is in an open configuration, in which the splint is not closed around the elbow of the arm of the patient, and when the splint is closed around the elbow of the arm of the patient.

19. The splint of claim 2, wherein the sleeve comprises a body that extends from a first edge to a second edge, and wherein the preformed opening is formed within the body of the sleeve, such that the presized perimeter of the preformed opening is spaced apart from both the first edge and the second edge.

20. The splint of claim 2, further comprising at least one anchor point configured to selectively couple the splint to a restraint, to maintain the arm of the patient in a substantially fixed orientation relative to an external object.

* * * * *

UNITED STATES PATENT AND TRADEMARK OFFICE
CERTIFICATE OF CORRECTION

PATENT NO. : 10,188,541 B2
APPLICATION NO. : 15/003513
DATED : January 29, 2019
INVENTOR(S) : William Miles Combs Page 1 of 1

It is certified that error appears in the above-identified patent and that said Letters Patent is hereby corrected as shown below:

In the Claims

Claim 16, Column 17, Line 7, after "that faces the" please delete "win" and insert --arm-- therefor.

Signed and Sealed this
Ninth Day of April, 2019

Andrei Iancu
*Director of the United States Patent and Trademark Office*